US009497981B2

(12) United States Patent
Fahrenholz et al.

(10) Patent No.: US 9,497,981 B2
(45) Date of Patent: Nov. 22, 2016

(54) MEDICATED PARTICULATE ANIMAL FEED SUPPLEMENTS AND METHODS OF PREPARATION

(71) Applicant: Phibro Animal Health Corporation, Teaneck, NJ (US)

(72) Inventors: Charles Hollett Fahrenholz, Lee's Summit, MO (US); Ian John Francis Wilkinson, Ridgewood, NJ (US)

(73) Assignee: Phibro Animal Health Corporation, Teaneck, NJ (US)

( * ) Notice: Subject to any disclaimer, the term of this patent is extended or adjusted under 35 U.S.C. 154(b) by 548 days.

(21) Appl. No.: 13/920,542

(22) Filed: Jun. 18, 2013

(65) Prior Publication Data

US 2014/0004195 A1    Jan. 2, 2014

Related U.S. Application Data

(60) Provisional application No. 61/665,704, filed on Jun. 28, 2012.

(51) Int. Cl.
*A23K 1/17*     (2006.01)
*A61K 9/14*     (2006.01)

(52) U.S. Cl.
CPC ............. *A23K 40/10* (2016.05); *A23K 20/158* (2016.05); *A23K 20/195* (2016.05); *A23K 50/75* (2016.05); *A61K 9/143* (2013.01)

(58) Field of Classification Search
None
See application file for complete search history.

(56) References Cited

U.S. PATENT DOCUMENTS

| 3,019,109 | A | * | 1/1962 | Klothen | ................... | A23K 1/17 |
| | | | | | | 424/693 |
| 3,696,189 | A | | 10/1972 | Snyder | | |
| 4,015,018 | A | * | 3/1977 | Glabe | ...................... | A23K 3/03 |
| | | | | | | 426/2 |
| 4,211,781 | A | | 7/1980 | Chapman | | |
| 4,258,031 | A | * | 3/1981 | Tollett | ..................... | A23K 1/17 |
| | | | | | | 424/115 |
| 4,447,421 | A | * | 5/1984 | Klothen | ................. | A23K 1/002 |
| | | | | | | 264/117 |

(Continued)

FOREIGN PATENT DOCUMENTS

EP         0 041 114       12/1981
ES           501984         5/1981

(Continued)

OTHER PUBLICATIONS

Netafim (http://www.netafimusa.com/files/literature/wastewater/Mesh-vs-Micron.pdf, accessed Sep. 29, 2015, 1 printed page.*

(Continued)

*Primary Examiner* — Isaac Shomer
(74) *Attorney, Agent, or Firm* — Klarquist Sparkman, LLP

(57) ABSTRACT

The present invention is a process and the product produced by that process for solid, particulate animal feed premixes, characterized by having a certain particle size range, physical stability, hardness range, and rapid dissolution, wherein the premixes contain various drugs and other, pharmaceutically and nutritionally acceptable diluents, binders and formulation aids as needed, or desired.

19 Claims, 5 Drawing Sheets

(56) References Cited

U.S. PATENT DOCUMENTS

| | | | |
|---|---|---|---|
| 4,536,494 A * | 8/1985 | Carter | A23K 20/195 |
| | | | 514/31 |
| 5,053,235 A * | 10/1991 | Alley | A23K 50/20 |
| | | | 426/623 |
| 5,256,419 A * | 10/1993 | Roe | A01N 25/16 |
| | | | 252/88.1 |
| 5,683,739 A | 11/1997 | Lanter et al. | |
| 5,874,102 A * | 2/1999 | LaJoie | A23K 1/005 |
| | | | 424/438 |
| 5,997,939 A * | 12/1999 | Moechnig | A23K 1/004 |
| | | | 424/438 |
| 6,761,899 B1 | 7/2004 | Winstrom et al. | |
| 2006/0148653 A1 * | 7/2006 | Keller | A01N 25/08 |
| | | | 504/367 |
| 2010/0135934 A1 * | 6/2010 | Deckner | A61K 8/25 |
| | | | 424/57 |
| 2011/0318448 A1 * | 12/2011 | Rudd | A23K 20/24 |
| | | | 426/1 |

FOREIGN PATENT DOCUMENTS

| | | |
|---|---|---|
| ES | 2 094 315 | 12/1992 |
| NZ | 243341 | 5/1993 |

OTHER PUBLICATIONS

Roughage Buster (https://service.admani.com/portal/page/portal/ADM_Alliance_Nutrition/Departments/Sales%20%20Marketing/Beef/ProductInfo/S9344E%20RoughageBuster.pdf, accessed Sep. 29, 2015, 2 printed pages).*

SM Berge, LD Bighley, DC Monkhouse. "Pharmaceutical Salts." Journal of Pharmaceutical Sciences, vol. 66 No. 1, Jan. 1977, pp. 1-19.*

Terramycin 200—oxytetracycline hydrochloride powder Product Information, Phibro Animal Health Corporation, Jan. 2015.

* cited by examiner

MEDICATED PARTICULATE ANIMAL FEED SUPPLEMENTS AND METHODS OF PREPARATION

CROSS REFERENCE TO RELATED APPLICATION

This application claims priority from U.S. Provisional Application No. 61/665,704 filed on Jun. 28, 2012, which is incorporated by reference in its entirety herein.

FIELD OF THE INVENTION

The present invention relates to rapid dissolving, low dust particulate or granular medicated animal feed supplements and methods for making the same.

BACKGROUND OF THE INVENTION

Antibiotics, such as tetracyclines, are used as overall health promoters in livestock animals, and for therapeutic and prophylactic disease control in animals such as poultry and livestock, companion animals, and so forth. Such antibiotics are typically formulated in an animal medicated feed premix or animal feed supplement containing the antibiotic and an edible carrier. These premixes or animal feed supplements may then be mixed with a sufficient quantity of an appropriate animal feed to provide a final animal feed formulation having the desired level of active compound in the feed.

One problem associated with animal feed medication pertains to the loss of finely divided antibiotics through dusting and electrostatic adhesion of finely divided particles, which may cause a lack of uniformity in drug concentrations in the final feed from batch to batch. Dust particles that adhere to feed mills or other feed processing equipment or that may be carried away in dust collection system may contain significant quantities of the active ingredient. This may cause the feed mixtures to have a lower concentration of the medicament desired. Dust adherent to the feed processing equipment and dust collected in a dust collection system that is recycled in subsequent batches may cause the feed mixtures produced in later batches to have a higher concentration of the active ingredient than desired, or may cause carry over of the drug to feed batches which are not intended to contain the drug.

Many attempts have been made to overcome the problem of dust formation in animal feed premixes and supplements. For example, it is known to add oil to reduce the dust and electrostatic adhesion in animal feed supplements. In U.S. Pat. No. 4,211,781, there is taught a process for preparing a substantially dustless carbadox animal feed premix by admixing carbadox with a non-toxic oil and an edible carrier. In U.S. Pat. No. 3,696,189, it is taught to coat the antibiotic particles of an animal feed supplement with an oil to stabilize the antibiotic against the deleterious effects of moisture or other materials contained in the animal feed supplement. It is also known to add oil as a pharmaceutically and nutritionally acceptable carrier or diluent for animal feed supplements.

Another attempt to overcome the problem of feed batch cross contamination is taught in U.S. Pat. No. 4,447,421, directed to a process for making particulated (granulated) animal feed premixes by combining the drug with a compressible carrier, followed by blending the mixture, compressing the mixture, and granulating the composition. Although this process has been somewhat successful in reducing dusting, it would be desirable to reduce dusting further. Attempts have been made to do so through the addition of oil, however, it has been found that the addition of oil causes a loss of structural integrity of such compressed formulations and causes a separation of the drug from the carrier.

In another attempt, a substantially dustless solid animal feed premix is taught in U.S. Pat. No. 6,761,899 which is prepared by combining fermentation solids resulting from reduction of a fermentation broth including a fermentation medium in which an organism was cultured for producing the antibiotic, said fermentation solids having an antibiotic activity sufficient to ameliorate an antibacterial infection to treat an animal. This process requires the handling of live cultures and 4-5 days of processing to produce a dry material suitable for sizing before use.

SUMMARY OF THE INVENTION

The present invention is a process for the preparation of solid, particulate animal feed premixes, characterized by having a certain particle size range, hardness range, and rapid dissolution, wherein the premixes contain various drugs and other, pharmaceutically and nutritionally acceptable diluents, binders and formulation aids as needed, or desired.

The particulates or granules of the present invention contain a therapeutically active agent or supplement for addition to animal feed. The particulates of the present invention are prepared by the process comprising the steps of: adding roughage (dietary fiber) into a mixer; adding an inorganic carrier into the roughage while mixing; adding a therapeutically active agent while mixing; continue mixing until it is uniform; compacting the mixture to form a solid material; milling the solid to form particles; screening the particles to obtain particles of the preferred size for the active ingredient, e.g. from about 1000 μm to about 50 μm.

Feed mills in which medicated animal feed premixes, supplements, concentrates or finished medicated animal feeds are prepared, have a tendency to retain some of the finely divided therapeutic agents due to electrostatic adhesion, dusting or some other phenomenon associated with the day-to-day operation of such installations. The retention of therapeutic agents within the mill is obviously undesired since it may, and usually does, result in the contamination of subsequent batches of the same therapeutic agent, non-medicated or differently medicated animal feed or supplement prepared in said mill.

The present invention provides a process for the preparation of a granular product that prevents excessive build up, deposition, retention and/or dusting of therapeutic agent or mixture of therapeutic agents in a feed mill or in any other equipment used for the preparation of the above animal feed products, which would result in the contamination of same with said therapeutic agents while traversing said mill or other equipment in the course of being prepared; and provides stable granules that will resist break down to smaller particles and dust formation and also resist agglomeration forming larger particles while providing a vehicle for the rapid dissolution of the therapeutic agent. Throughout this specification and claims, the terms granule and particle are used interchangeably to refer to the same physical entity. The Granules of the present invention flow more evenly and more freely than powders through animal feed processing equipment resulting in improved flowability. The smaller surface area per gram of the granules and fiber content of the granules results in a physically and chemically stable product.

The particles of the premixes obtained by the process of the present invention are designed to be of a size range to ensure flowability through measuring and mixing equipment, and not to adhere to processing equipment surfaces (or to packaging surfaces as for instance by electrostatic adhesion, or to be carried away in a dust collecting stream, and yet at the same time to be of an adequately small size and size range so that a statistically sufficient number of particles are present in the finished feed premix to assure uniform distribution throughout the batch of feed in which it is blended to achieve the desired therapeutic agent concentration. The present invention thus provides medicated animal feed additives in a solid particulate or granular form having improved resistance to powdering and good fracture toughness. The present invention also provides a method of producing animal feed compositions.

DETAILED DESCRIPTION OF THE INVENTION

Figure 1:
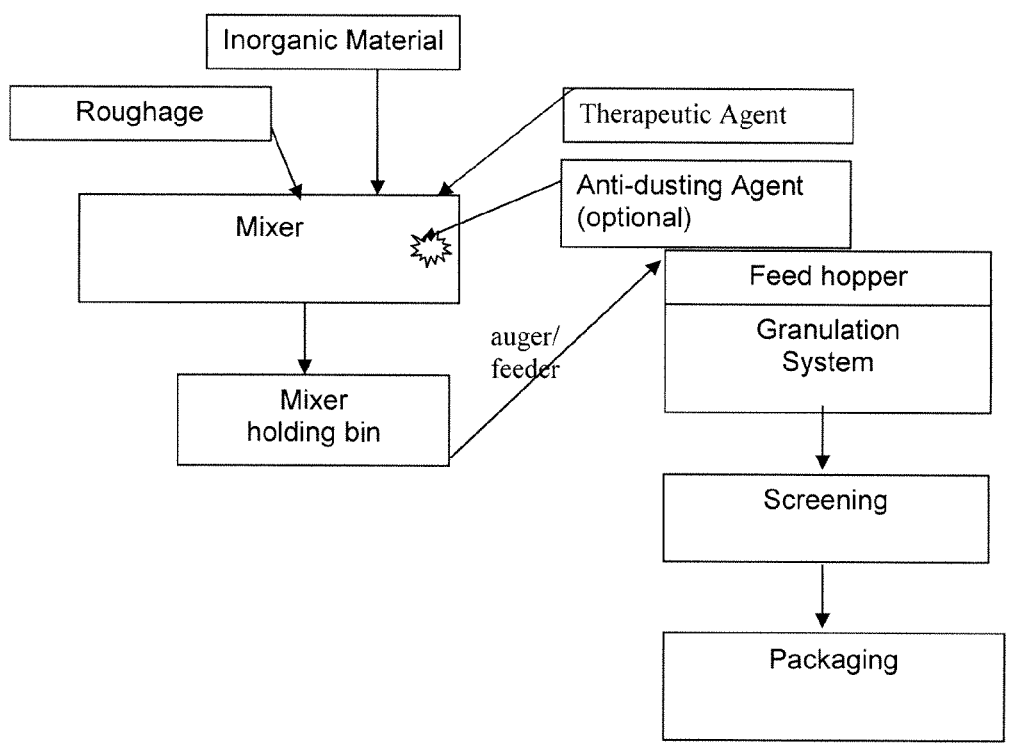
FIG. 1 is a diagrammatic illustration of an exemplary method of manufacturing a particulate animal feed supplement of the present invention.
Figure 2:
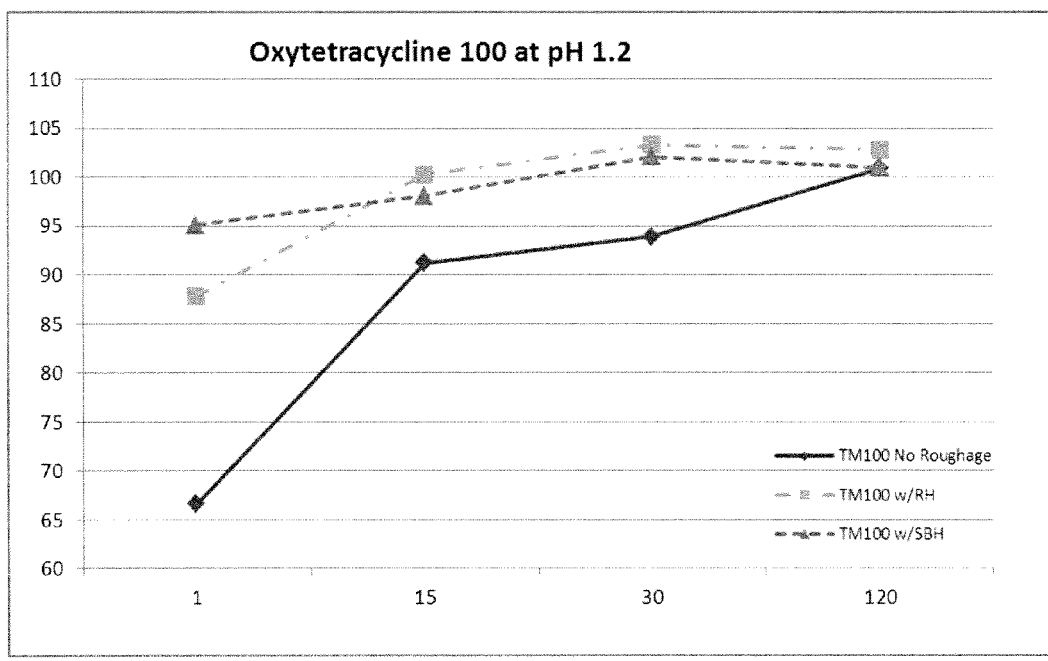
FIG. 2 Shows percentage of target potency dissolved at each time interval for granular oxytetracycline 100 g/lb product at a pH 1.2 level. The horizontal axis is the testing time points in minutes and the vertical axis is the percentage of target potency measured.
Figure 3:
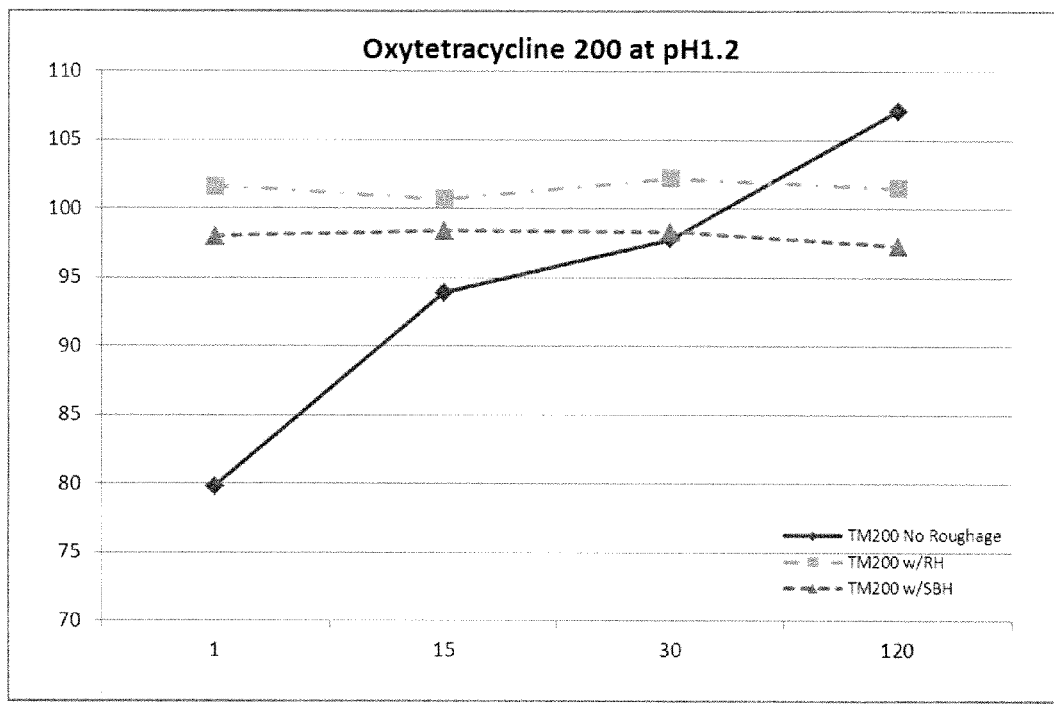
FIG. 3 Shows percentage of target potency dissolved at each time interval for granular oxytetracycline 200 g/lb product at a pH 1.2 level. The horizontal axis is the testing time points in minutes and the vertical axis is the percentage of target potency measured.
Figure 4:
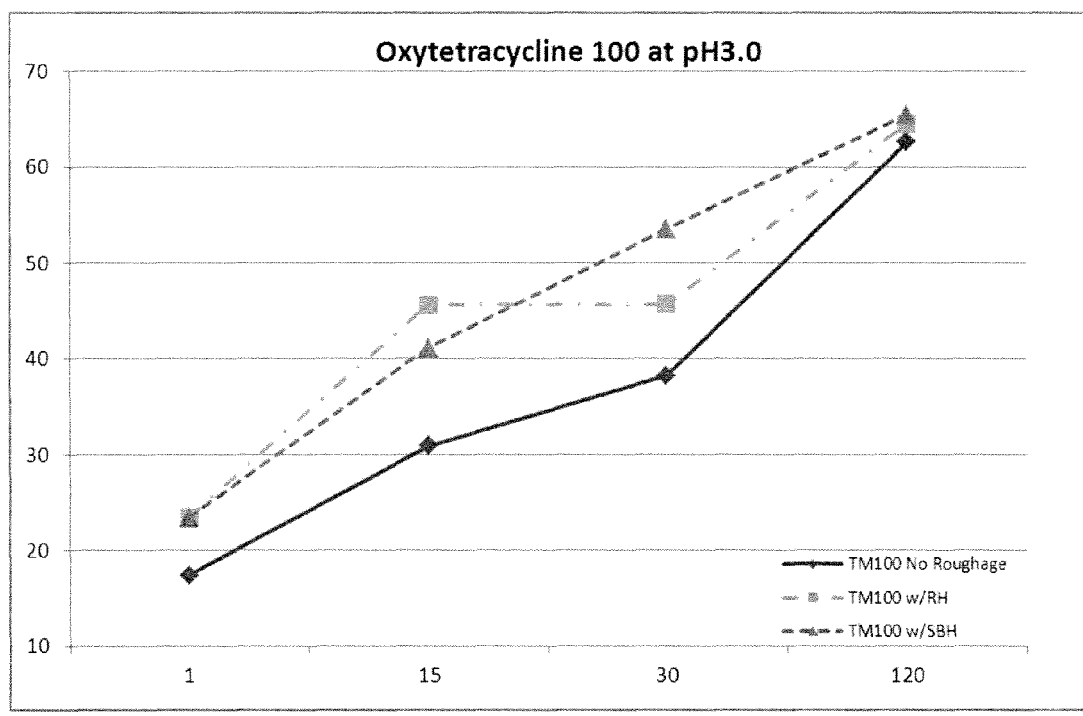
FIG. 4 Shows percentage of target potency dissolved at each time interval for granular oxytetracycline 100 g/lb product at a pH 3.0 level. The horizontal axis is the testing time points in minutes and the vertical axis is the percentage of target potency measured.
Figure 5:
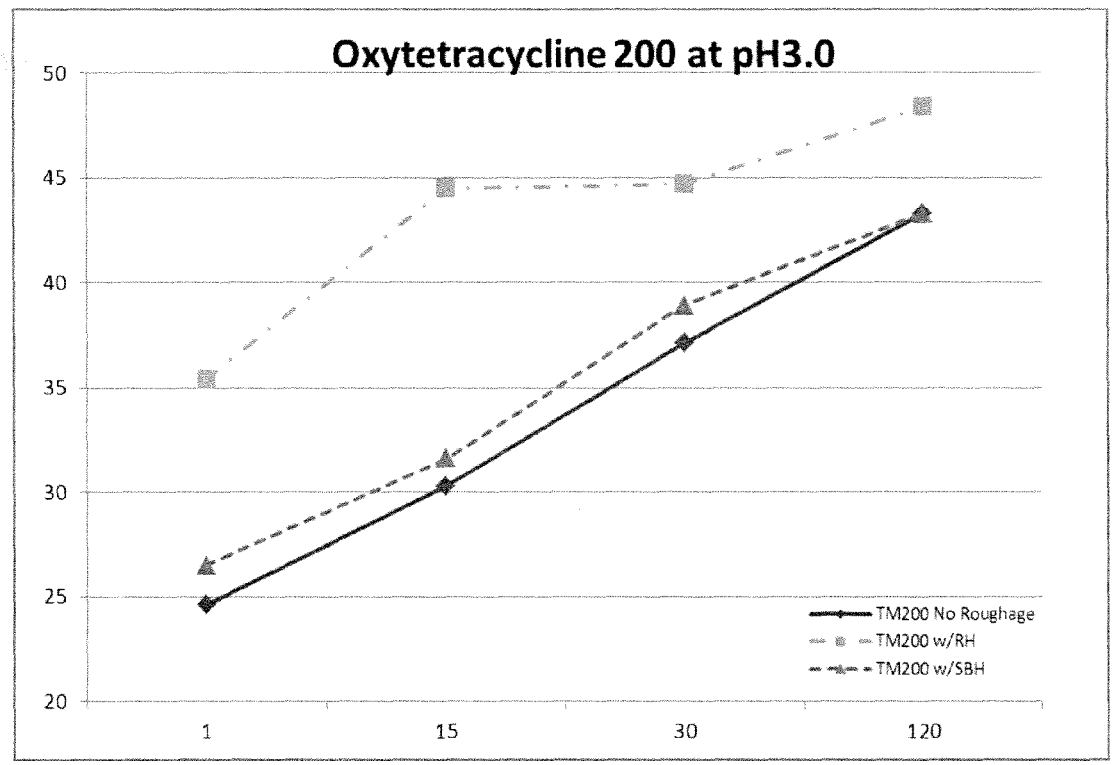
FIG. 5 Shows percentage of target potency dissolved at each time interval for granular oxytetracycline 200 g/lb product at a pH 3.0 level. The horizontal axis is the testing time points in minutes and the vertical axis is the percentage of target potency measured.

In a preferred embodiment, the granulation of the present invention containing a therapeutic agent in a fiber containing granule is prepared by the process comprising the steps of: adding roughage (dietary fiber) into a mixer; adding an inorganic material while mixing; adding an optional anti-dusting agent adding therapeutically active agent while mixing; continue mixing until the mixture is uniform; compacting the mixture to form a solid material; milling the solid material to form particles; screening the particles to obtain particles sized from about 1000 μm to about 50 μm.

The compacting step forms a solid from the powder materials. The solid may be in the form of ribbons or molded shapes. The milling step reduces the solid to particles having the nominal particle size of about 1200 μm or less. The milled particles are then screened to remove particulates having a nominal particle size greater than about 1000 μm and less than about 50 μm. Particles removed are returned to the beginning of the granulation step and processed again with additional virgin blended material or in the mixing step as part of a new batch.

The therapeutic agent may be selected from the group comprising antibiotics, antibacterials, anticoccidials, and antihelmetics. A preferred antibiotic will be selected from the group consisting of tetracyclines. Non-limiting examples of tetracyclines include the naturally occurring tetracyclines such as: tetracycline, chlortetracycline, chlortetracycline calcium, oxytetracycline and demeclocycline; and the semi-synthetic tetracycline such as: doxycycline, lymecycline, meclocycline, methacycline, minocycline, and rolitetracycline and their salts and hydrates acceptable for pharmaceutical or veterinary use including acid addition salts, hydrates, metal complexes and salts thereof, including calcium complexes. Additional preferred therapeutic agents would be amprolium, carbadox, chlortetracycline, neomycin (and combinations), nicarbazin, pyrantel tartrate, salinomycin, semduramicin, and virginiamycin. The most preferred antibiotic is oxytetracycline.

As used herein, the term therapeutic agent is intended to encompass, the free base, salts of therapeutic agents acceptable for pharmaceutical or veterinary use including acid addition salts, and metal complexes and salts thereof, including calcium complexes.

Roughage materials may include without limitation one or more of the following: Almond Hulls, Psyllium Seed Husk, Dried Apple Pectin Pulp, Malt Hulls, Dried Apple Pomace, Clipped Oat By-Product, Bagasse, Oat Hulls, Barley Hulls, Oat Mill By-Product, Barley Mill By-Product, Peanut Hulls, Dried, Plain Beet Pulp, Rice Hulls, Buckwheat Hulls, Rice Mill By-Product, Dried Citrus Meal, Rye Mill Run, Dried Citrus Pulp, Soybean Hulls, Citrus Seed Meal, Soybean Mill Feed, Com Cob Fractions, Soybean Mill Run, Cottonseed Hulls, Sunflower Hulls, Flax Straw By-Product, Ground Straw, Ground Corn Cob, Dried Tomato Pomace.

Roughage (fibrous material) preferred in the present invention is generally from grain and usually consists of the outer covering of the grain but may include other parts of the grain generated during the grain milling process. Examples of roughage preferred in the present invention include, rice hulls, soybean hulls, oat hulls, corn cob fractions, ground corn cob, wheat bran, and the like. The most preferred roughage of the present invention is rice hulls.

Inorganic material as used in this invention is a material that is composed of minerals, or made from minerals, not animal or vegetable in origin, that is compressible in the absence of other materials, or binders, and is pharmaceutically inert. A non-limiting list of inorganic materials useful in the present invention includes silicates, calcium and magnesium salts, calcium carbonate, oyster shell meal, calcium sulphate.

FIG. 1 is a flow diagram outlining the process according to the present invention. A particulate composition of the present invention is made by the following process. Add required quantity of rice hulls to the mixer. Then start mixing. While mixer is mixing, add calcium carbonate to the mixer. A portion may be held back to adjust to the targeted batch weight. While mixing, add mineral oil, if required. While mixing, add the required quantity of oxytetracycline dihydrate to the mixer. While mixing, add the remaining quantity of calcium carbonate (if applicable). Once all raw materials are in the mixer, mix for the time required to achieve a homogeneous blend. Then stop mixing. When the mixer and holding bin are ready, open the bottom gate and keep the mixer running until mixer is empty. Then stop the mixer. For the granulation, start any equipment necessary to move material to the feed hopper for the granulation system. When the feed hopper has a sufficient quantity of blended material present, start the granulation system. If there are multiple blends per lot, repeat the dry blend steps above, before all of the previous blended material is consumed. Run the granulation system continuously, screening the particulates to obtain the desired nominal particle size range. Package into approved containers.

Dry Blend:

Add a measured quantity of roughage to the mixer, then start mixing. While mixer is mixing, add a measured quantity of inorganic material to the mixer. A portion of the inorganic material may be held back to adjust to the targeted batch weight. While mixing, if dusting is occurring, an optional anti-dusting agent, may be added. While mixing, add the required quantity of therapeutic agent to the mixer. While mixing, add the remaining quantity of inorganic material (if applicable). Once all raw materials are in the mixer, mix until a homogeneous blend is obtained. Then stop mixing. Transfer the mixture to the input of the roll compactor. It is necessary to increase the density of the mixture, that is to remove air, prior to compacting. The powder mixture will not compress properly if air is not removed. The compactor input process increases the density of the mixture. This can be achieved with a dual screw feed or auger design or their functional equivalent all of which are commercially available and known to those skilled in the art. Transfer the mixture to the input of the roller compactor. The compactor will produce compacts which, depending on the type of compactor, will be in the shape of ribbons, pellets or bars. The shape of the compacted material will depend on the rollers used. The compacted material is then milled through an impact, compression, shear, or attrition mill to obtain particulates. The particulates are then screened to obtain particulates of the preferred particle size and size distribution.

In a preferred embodiment, add a measured quantity of rice hulls to the mixer, then start mixing. While the mixer is mixing, add calcium carbonate to the mixer. A portion may be held back to adjust to the targeted batch weight. While mixing, add mineral oil, to prevent dusting if required. While mixing, add the required quantity of oxytetracycline dihydrate to make a product having the desired strength of therapeutic agent per unit weight of the final product to the mixer. While mixing, add the remaining quantity of calcium carbonate (if applicable). Once all raw materials are in the mixer, mix until a homogeneous blend is formed. Then stop mixing. Transfer the mixture to the input of a roller compactor. The compactor input increases the density of the mixture. This may be achieved with a number of compactor input designs such as with a hopper agitator or dual screw feed or other auger designs. The compactor will produce compacts in the shape of ribbons. The ribbon is then milled through a mill such as a lump or flake breaker to obtain large particles. Which are subsequently milled to the desired particle size range. The resulting particulates are then screened to obtain particulates of the preferred particle size and size distribution having a nominal particle size in the case of oxytetracycline, at a dose of 200 g/lb, between about 1000 µm and about 50 µm. See Table 1 for a broader understanding of the dosage (concentration of therapeutic agent in the granulation) to particle size relationship. Oversized and undersized particles removed by screening are returned to the beginning of the granulation process, combined with fresh material and granulated again or as part of a continuous process or a new batch.

Mixing System

This is used to preblend the dry ingredients and the optional anti-dusting agent such as mineral oil, soybean oil and similar long shelf life edible oils prior to granulation. Long shelf life of the oil is defined as being stable, edible, for at least 2 years at room temperature. Typically this is done with a paddle or ribbon blender. However, any centrifugal blender will work for this step. The requirement is to ensure that each of the materials are suitably dispersed.

Granulation System Design and Operation:

In a design of the granulation system such as a FitzPatrick system, which uses a dual screw infeed system to feed the compaction rolls and increase the density of the powder mixture, such that when the product mixture enters the main compaction rolls their sole function is to compress powder to a smaller and smaller volume until it reaches a maximum pressure at the nip of the rolls.

An alternate design of infeeding to the compactor is used by Bepex Hosokawa that utilizes an auger inside the feed hopper directly that increases the density of the material prior to it entering the main compaction rolls where the same final compaction process is completed.

In either case, if a significant amount of air were still present in the powder the material would fail to compress properly, so although the densification process is critical to proper compaction, it can be achieved by at least two different designs of the infeed system.

Once the material has been compressed, the material falls from the underside of the compaction rolls in compressed sheets (flakes) of product into a number of flake breaking and milling steps. The number of flake breaking and milling steps in the process will depend on the design of the equipment. As a minimum there will be one "flake breaker" followed by one mill before the product is screened for in specification material. Typically, the screening step will involve a double screen that removes both oversized and undersized (fines) material. The over and undersized material is returned to the compaction feed hopper for reintroduction into the granulation system. If just oversized material is screened, the material could be either returned to a mill directly or inclusion in the granulation step again, through a recycle loop, where it is combined with virgin blended material prior to granulation. If fines are included in the mix, then the material will be returned for regranulation and combined with virgin blended material prior to going through the granulation process again.

In any scenario, one of the outputs from the screening is the finished product which will be packaged. This is the material between the two screens that does not get recycled back to the beginning of the granulation process or the material from below the single screen when a single screen is used.

From above, once the material has been compressed the flake breaker, mill and screener that are suitable can vary significantly. The type of mill typically used for this type of system is a hammer mill, of which there are many suppliers. Similarly there are many manufacturer's of flake breakers that would be suitable for this type of system. The intent of the flake breaker is to produce large, manageable pieces of compressed material for the mill to breakdown into the desired size range. The type of screener used is typically a flat vibratory screener (typical manufacturer's are Rotex and Kason) which provides a large surface area and screening time to ensure suitable particle size separation. Particle sizes are measured according to ANSI/ASAE Standard 5319.4, 'Method of Determining and Expressing Fineness of Feed Material by Sieving."

Particle Size

The particle size produced by a system as described above is in reality a range of particle sizes between the upper and lower screens. In principle, any production such as this is looking to have the largest particle size range that would be reasonably attainable, when balanced with the other requirements for the product granule, as described below in this section. This is for a number of reasons;

- The larger the particle size within the range, the more flowable the product will be.
- The larger the granule the more physically protected the therapeutic agent will be, if that is a desired trait for the product.
- The larger the granule the higher the productivity for the product during production, i.e. kilograms per hour production rate is higher.
- The smaller the granule, the easier it is to ensure a suitable distribution of therapeutic agent in the finished feed.

However, the required particle size range is dependant on the bulk therapeutic agent being manufactured and the concentration of that product. For example Oxytetracycline (OTC) at 200 g/lb requires a particle size range that is less than about 1000 μm. The reason for this is that, for particle sizes greater than about 1000 μm, given the OTC dosage per gram of granules, the amount of OTC in each particle could be so large that when mixed with feed ingredients to produce the final medicated feed, the presence of one extra large particle would be sufficient to provide an inappropriate dose of OTC to the animal or cause the dissolution results to be out of range. It is very difficult to distribute a few large particles of therapeutically active drug evenly amongst bulk feed such that a small sample of such feed would be representative of the batch.

TABLE 1

Relationship of Granule Size, Concentration of Therapeutic Agent and Therapeutic Dose

| Therapeutic Agent Concentration In The Granules in Grams/Pound | Therapeutic Agent Concentration In Finished Feed in Grams/Ton | Therapeutic Agent Granules Preferred Particle Size Range |
|---|---|---|
| <50 | <50 | about 50 μm to about 900 μm |
|  | 50 to <100 | about 50 μm to about 1200 μm |
|  | 100 to <250 | about 50 μm to about 1500 μm |
|  | >250 | about 50 μm to about 1800 μm |
| 50 to <150 | <75 | about 50 μm to about 900 μm |
|  | 75 to <150 | about 50 μm to about 1100 μm |
|  | 150 to <350 | about 50 μm to about 1300 μm |
|  | >350 | about 50 μm to about 1600 μm |
| 150 to <300 | <100 | about 50 μm to about 900 μm |
|  | 100 to <200 | about 50 μm to about 1000 μm |
|  | 200 to <400 | about 50 μm to about 1200 μm |
|  | >400 | about 50 μm to about 1300 μm |

Other therapeutic agents that have either a lower final concentration in their premix, e.g. 100 g/lb, or have a higher concentration final dosage in the finished feed, can have different particle size specifications in order to meet the characteristics of their particular therapeutic dosage ranges. Table 1 illustrates the relationship between therapeutic agent concentration, therapeutic dose and particle size.

The technology here would be applicable to all particle size ranges as the intent is not to be limited to one particle size range, but address the fact that once in the granule, the therapeutic agent is "trapped" within the granule complex, until such time as the granule breaks down and releases the drug.

Granulation Inert Ingredients:
Chemical

In addition to particle size, the rate of dissolution (granule breakdown) can be affected by the inorganic material used. We have primarily used calcium carbonate, which we have found to have good compressibility and the ability to hold together as a granule. However, other carriers can also be used, such as calcium sulphate. In general, the main carrier will be an inert, mineral based material (i.e. non-organic). Each of these carriers will respond differently to dissolution in the animal gut due to their specific chemical characteristics. However, in each case relative to itself as a powder versus itself as a compressed granule, for any given inorganic material (mineral carrier) the relative dissolution time of the therapeutic agent availability would be improved, match dissolution times of the powder, by including an organic carrier, roughage, in the granule matrix.

Within the livestock animal industries, one could classify in two general categories the manner in which the premixes are used; low-tech and mechanized. In the low-tech world most of the premixes are added to the finished feed using hand scoops and weighed out individually. In the mechanized world the premixes and other ingredients are weighed into the final feed blend using micro metering machines. These are generally one form or another of a weighing system that feeds the material into a blender through a small auger until a set weight of material has been added for a given weight of feed.

In the low tech facilities, the nature/form of the premix is much less important than the cost of the premix and hence they tend to use non granular products where they are available.

However, in the mechanized facilities, the nature/form of the premix is much more critical. Flowability becomes much more important because any disruption to flow could result in an incorrect dosage to the feed blender and ultimately not dosing the animals correctly. Proven flowability allows for less direct supervision and more reliability of the mixing processes, which leads directly to improved productivity at the feed mills. In addition, reduction in dustiness is also part of the overall customer perspective because they are emptying whole bags into a hopper, there is plenty of room for dust clouds and the resulting house keeping issues this can create.

In general, with the consolidation of the livestock industries, the move to mechanized feed mills is increasingly important. Therefore, the nature of the premix has become more and more important to our customers. For OTC there has never been a granular premix in the market. However, for other products such as chlortetracycline (CTC) granular products have been around for more than 20 years and are part of the basic requirements for many who use CTC or would like to switch to an alternate tetracycline.

Bio-Equivalence

The inventive products have demonstrated in vitro biological equivalence compared to the powder, non-granulated product. This was done by testing the dissolution rate of the inventive granular OTC product at 3 different pH levels when compared with the current commercially available powder form. As can be seen in the attached data, for any given pH the powder and granular OTC resulted in equivalent OTC potency. However, the potency at the pH 2 was significantly higher than other pH's. It is considered pH 2 is more representative of the pH in the gut of many species the gut than the other pH levels. Also, OTC is generally more soluble in acidic environments. Throughout the specification, the term extracted and the term dissolved are used interchangeably and have the same meaning.

This study was conducted in order to demonstrate the bioequivalence of inventive Oxytetracycline granular and non-inventive powder formulations made from the same ingredients. The two formulations have the same active ingredient and excipients in their composition.

The bioequivalence of two Oxytetracycline formulations, one granular and one powder was established by comparing the Oxytetracycline dissolution at three pH levels 1.2, 4.6 and 7.4, which simulate the range found in the intestinal tract, at two and six hours which is representative of the contact intervals in the avian, porcine and bovine GI track.

Two sample lots of Oxytetracycline feed supplement were prepared. Each lot of material contained the same ingredients in the same amounts. Sample 1 was prepared by the conventional process of mixing the ingredients forming a powder mixture. Lot Sample 2 was prepared by the inventive process to form granules having a particle size range from 1000 µm to 50 µm.

Oxytetracycline 200 g/lb was produced with the following formulation:

TABLE 2

Oxytetracycline 200 g/lb Formulations

| Components | Nominal Potency (g/lb) | Sample 2 Weight (lbs) Per 1,000 lbs | Sample 1 Weight (lbs) Per 1,000 lbs |
|---|---|---|---|
| Oxytetracycline Dihydrate | 422.2 | 473.7 | 473.7 |
| Mineral oil | 454.0 | 50.0 | 0 |
| Rice hulls | 454.0 | 80.0 | 80 |
| Calcium Carbonate (q.s.) | 454.0 | q.s. | q.s. |

The process used for the inventive product utilized roll compaction. First a powder blend of all of the necessary ingredients was made as described in the general procedure. The powder was then compressed under high pressure between two rolls. The material was transformed into a rock hard sheet of material that was then broken down though a milling and screening process into granules. The final step was to screen the product and any material that is outside the desired range was returned to the start of the granulator and was reincorporated into the compaction and granulation process.

One sample lot of each type of formulation, granule and powder was used. Each sample was analyzed for Oxytetracycline content concurrently with the 2 hour analysis. Each sample was evaluated at each pH in triplicate. The samples were weighed and a known amount of pH buffer added. The samples were shaken on a reciprocating shaker for 2 or 6 hours. The resulting sample solution was filtered into an auto-sampler vial and analyzed by HPLC for Oxytetracycline content. The results for the powder were compared to those for the granular forms at each pH and time interval.

Each granule sample met the established guideline for bioequivalence to the FDA approved powder formulation which is ±20% for each data point, therefore establishing bioequivalence of the inventive granule to the powder. This study was conducted according to current Good Manufacturing Practices as set forth in 21 CFR Part 210-211.

TABLE 3

Standards Used.

| Compound | Lot Number | Purity |
|---|---|---|
| Oxytetracycline | J1J172 | 900 µg/mg |
| Tetracycline | 126K0734 | 99% |

Oxytetracycline is used for quantization. Tetracycline is used as a resolution standard in system suitability.

TABLE 4

Sample Lots Used In This Comparison.

| Lot ID | Lot Description |
|---|---|
| Sample 2 | Inventive |
| Sample 1 | Powder |

Experimental Design

Three pH buffers were prepared at 1.2, 4.6 and 7.4 according to USP guidelines. For the 2 hour interval, 9 total sample replicates were prepared (3 for each pH level) for each sample by accurately weighing approximately 0.56 grams and transferring to a 250 mL plastic bottle. Two hundred milliliters (200 ml) of each pH buffer will be added to three accurately weighed portions of each lot. The samples were then placed on a reciprocating shaker for 2 hours. Following 2 hours, a portion of each solution was filtered through an IC Acrodisc 0.45 µm syringe filter into an HPLC vial. The solutions were then analyzed using method described below with triplicate injections.

The above procedure was repeated after 6 hours of shaking for a separate set of accurately weighed portions of each product lot. The amount of Oxytetracycline found in each sample was calculated and the average amount at each pH level and time interval. The average results were compared between the two formulations. In addition, a percent of premix assay was calculated by dividing the amount found in the shaken sample by the premix assay result and multiplying by 100%.

Dissolution Procedure

The three pH buffers were prepared at pH 1.2, 4.6, and 7.4 according to USP guidelines ("Buffer Solutions").

For the 2 hour interval, 9 total sample replicates were prepared, 3 for each pH level for each pH level, for each sample by weighing accurately about 0.56 grams and transferring the sample to a 250 ml plastic bottle. Two hundred milliliters (200 ml) of each pH buffer were added to three weighed samples. The samples were then placed in a reciprocating shaker for 2 hours. Following 2 hours, a portion of each solution was filtered through an IC Acrodisc 0.45 µm syringe filter into an HPLC vial. The solutions were then analyzed in triplicate.

For the 6 hour interval, 9 total replicates were prepared, 3 for each pH level, for each sample by weighing accurately about 0.56 grams of sample and transferring the sample to a 250 ml plastic bottle. Two hundred milliliters (200 ml) of each pH buffer were added to three weighed samples. The samples were then placed in a reciprocating shaker for 6 hours. Following 6 hours, a portion of each solution was filtered through an IC Acrodisc 0.45 µm syringe filter into an HPLC vial. The solutions were then analyzed in triplicate for oxytetracycline. When the term oxytetracycline is used throughout the specification and claims, it refers to the oxytetracycline base.

The average amount of oxytetracycline found for each pH level and time interval was compared between the inventive granule and the non-inventive powder formulation. At every point of comparison, the inventive granule was bioequivalent to the powder.

Initial Analysis Results

Each sample was initially analyzed according to the method for Oxytetracycline.

TABLE 5

Initial Assay Results for Oxytetracycline.

| Sample ID | Oxytetracycline HCl (g/lb) |
|---|---|
| 2 | 199.3 |
| 1 | 185.3 |

TABLE 6

Two Hour Dissolution Results are presented below.

| Sample ID | pH | Oxytetracycline HCl g/lb | Percent of Premix Assay |
|---|---|---|---|
| 0002 A | pH 1.2 | 202.3 | 101.5 |
| 0002 A | pH 1.2 | 202.2 | 101.5 |
| 0002 A | pH 1.2 | 202.1 | 101.4 |
| 0002 B | pH 1.2 | 200.6 | 100.7 |
| 0002 B | pH 1.2 | 200.1 | 100.4 |
| 0002 B | pH 1.2 | 200.7 | 100.7 |
| 0002 C | pH 1.2 | 200.5 | 100.6 |
| 0002 C | pH 1.2 | 200.0 | 100.4 |
| 0002 C | pH 1.2 | 200.2 | 100.5 |

For all samples, the overall average, standard deviation and % RSD were calculated for each pH levels. The results are presented below.

TABLE 7

2 Hour Dissolution Standard Deviation and % RSD

| Statistic | Amount Found (g/lb) | Percent of oxytetracycline dissolved from Premix Assay |
|---|---|---|
| Overall Statistics for pH 1.2 | | |
| Average | 193.10 | 100.40 |
| STD Deviation | 8.15 | 0.59 |
| % RSD | 4.22 | 0.58 |
| Overall Statistics for pH 4.6 | | |
| Average | 49.76 | 25.93 |
| STD Deviation | 4.21 | 2.55 |
| % RSD | 8.45 | 9.85 |
| Overall Statistics for pH 7.4 | | |
| Average | 7.07 | 3.67 |
| STD Deviation | 0.94 | 0.40 |
| % RSD | 13.26 | 10.81 |

TABLE 8

Six Hour dissolution results are presented below.

| Sample ID | Sample pH | Oxytetracycline HCl g/lb | % of Premix Assay |
|---|---|---|---|
| 0002 A | pH 1.2 | 208.9 | 104.8 |
| 0002 A | pH 1.2 | 209.0 | 104.8 |
| 0002 A | pH 1.2 | 208.7 | 104.7 |
| 0002 B | pH 1.2 | 201.6 | 101.2 |
| 0002 B | pH 1.2 | 200.6 | 100.6 |
| 0002 B | pH 1.2 | 201.3 | 101.0 |
| 0002 C | pH 1.2 | 201.6 | 101.2 |
| 0002 C | pH 1.2 | 201.7 | 101.2 |
| 0002 C | pH 1.2 | 201.6 | 101.2 |
| Average | | 203.89 | 102.30 |
| Standard Deviation | | 3.74 | 1.88 |
| % RSD | | 1.84 | 1.84 |
| 0002 D | pH 4.6 | 61.4 | 30.8 |
| 0002 D | pH 4.6 | 61.4 | 30.8 |
| 0002 D | pH 4.6 | 61.1 | 30.7 |
| 0002 E | pH 4.6 | 59.3 | 29.8 |
| 0002 E | pH 4.6 | 59.4 | 29.8 |
| 0002 E | pH 4.6 | 59.3 | 29.7 |
| 0002 F | pH 4.6 | 58.9 | 29.5 |
| 0002 F | pH 4.6 | 58.8 | 29.5 |
| 0002 F | pH 4.6 | 58.7 | 29.5 |
| Average | | 59.81 | 30.01 |
| Standard Deviation | | 1.14 | 0.57 |
| % RSD | | 1.91 | 1.91 |
| 0002 G | pH 7.4 | 8.4 | 4.2 |
| 0002 G | pH 7.4 | 8.4 | 4.2 |
| 0002 G | pH 7.4 | 8.4 | 4.2 |
| 0002 H | pH 7.4 | 8.2 | 4.1 |
| 0002 H | pH 7.4 | 8.3 | 4.1 |
| 0002 H | pH 7.4 | 8.1 | 4.1 |
| 0002 I | pH 7.4 | 7.9 | 3.9 |
| 0002 I | pH 7.4 | 7.9 | 3.9 |
| 0002 I | pH 7.4 | 7.8 | 3.9 |
| Average | | 8.15 | 4.09 |
| Standard Deviation | | 0.25 | 0.13 |
| % RSD | | 3.06 | 3.06 |
| 0001 A | pH 1.2 | 185.0 | 99.8 |
| 0001 A | pH 1.2 | 185.1 | 99.9 |
| 0001 A | pH 1.2 | 184.9 | 99.8 |
| 0001 B | pH 1.2 | 185.7 | 100.2 |
| 0001 B | pH 1.2 | 185.2 | 99.9 |
| 0001 B | pH 1.2 | 185.5 | 100.1 |
| 0001 C | pH 1.2 | 185.7 | 100.2 |
| 0001 C | pH 1.2 | 185.8 | 100.3 |
| 0001 C | pH 1.2 | 185.3 | 100.0 |
| Average | | 185.35 | 100.03 |
| Standard Deviation | | 0.34 | 0.18 |
| % RSD | | 0.18 | 0.18 |
| 0001 D | pH 4.6 | 54.2 | 29.3 |
| 0001 D | pH 4.6 | 54.4 | 29.4 |
| 0001 D | pH 4.6 | 54.3 | 29.3 |
| 0001 E | pH 4.6 | 54.7 | 29.5 |
| 0001 E | pH 4.6 | 54.8 | 29.6 |
| 10001 E | pH 4.6 | 54.8 | 29.5 |
| 0001 F | pH 4.6 | 53.9 | 29.1 |
| 0001 F | pH 4.6 | 54.1 | 29.2 |
| 0001 F | pH 4.6 | 54.0 | 29.1 |
| Average | | 54.36 | 29.33 |
| Standard Deviation | | 0.34 | 0.18 |
| % RSD | | 0.63 | 0.63 |
| 0001 G | pH 7.4 | 6.8 | 3.7 |
| 0001 G | pH 7.4 | 6.8 | 3.7 |
| 0001 G | pH 7.4 | 6.8 | 3.7 |
| 0001 H | pH 7.4 | 6.7 | 3.6 |
| 0001 H | pH 7.4 | 6.6 | 3.6 |
| 0001 H | pH 7.4 | 6.7 | 3.6 |
| 0001 I | pH 7.4 | 6.9 | 3.7 |
| 0001 I | pH 7.4 | 6.8 | 3.7 |
| 0001 I | pH 7.4 | 6.8 | 3.7 |
| Average | | 6.78 | 3.66 |
| Standard Deviation | | 0.09 | 0.05 |
| % RSD | | 1.30 | 1.30 |

The overall average, standard deviation and % RSD were calculated for each pH level. The results are presented in Table 9 below.

TABLE 9

6 Hour Dissolution Standard Deviation and % RSD

| Statistic | Amount Found (g/lb) | Percent of oxytetracycline dissolved from Premix Assay |
|---|---|---|
| Overall Statistics for pH 1.2 | | |
| Average | 194.62 | 101.16 |
| STD Deviation | 9.88 | 1.75 |
| % RSD | 5.08 | 1.72 |
| Overall Statistics for pH 4.6 | | |
| Average | 57.09 | 29.67 |
| STD Deviation | 2.92 | 0.54 |
| % RSD | 5.12 | 1.82 |
| Overall Statistics for pH 7.4 | | |
| Average | 7.47 | 3.88 |
| STD Deviation | 0.73 | 0.24 |
| % RSD | 9.74 | 6.18 |

Summary Results

The average values found values for each sample at each pH level at each time-point were compared and a % difference calculated. This is presented below.

TABLE 10

Amount of Oxytetracycline Dissolved (g/lb)

| pH | Time-point | Sample 2 | Sample 1 | % Difference |
|---|---|---|---|---|
| 1.2 | 2 hour | 200.98 | 185.21 | 7.8 |
| 1.2 | 6 hour | 203.89 | 185.35 | 9.1 |
| 4.6 | 2 hour | 48.69 | 50.83 | -4.4 |
| 4.6 | 6 hour | 59.81 | 54.36 | 9.1 |
| 7.4 | 2 hour | 7.70 | 6.45 | 16.2 |
| 7.4 | 6 hour | 8.15 | 6.78 | 16.8 |

TABLE 11

Percent of Oxytetracycline Dissolved from Premix

| pH | Time-point | Sample 2 | Sample 1 | % Difference |
|---|---|---|---|---|
| 1.2 | 2 hour | 100.85 | 99.96 | 0.9 |
| 1.2 | 6 hour | 102.30 | 100.03 | 2.2 |
| 4.6 | 2 hour | 24.43 | 27.43 | -12.3 |
| 4.6 | 6 hour | 30.01 | 29.33 | 2.3 |
| 7.4 | 2 hour | 3.86 | 3.48 | 9.8 |
| 7.4 | 6 hour | 4.09 | 3.66 | 10.5 |

Conclusions

Each of the percent difference results between the inventive particulates (granules) met the protocol criterion of being within ±20% of the FDA approved powder product. Bio-equivalence was proven between the powder and granular formulations at three pH levels and two time periods.

Solubility

The inventive products have demonstrated that for any given inorganic material (mineral carrier) the relative dissolution time of the therapeutic agent is improved by including an organic carrier (roughage), in the granule matrix. This was demonstrated by incorporating in separate granule mixes rice hulls and soy hulls and comparing the dissolution of these granules to granules made without a roughage carrier.

Non-inventive oxytetracycline formulations containing an amount of oxytetracycline equivalent to oxytetracycline HCl 100 g/lb and Oxytetracycline HCl 200 g/lb granular materials were produced using the following formulation:

TABLE 12

Formulations Non-Inventive Premix

| Component | TM 100 Weight (lb)/1000 lb | TM200 Weight (lb)/1000 lb |
|---|---|---|
| Oxytetracycline dihydrate | 281.2 | 468.6 |
| Calcium carbonate | 715.7 | 481.4 |
| Mineral Oil | 50.0 | 50.0 |

Additionally four batches of premix were produced using the inventive process containing the roughage materials rice hulls or soy hulls according to the following formulations:

TABLE 13

Formulations of Inventive Premix

| | TM 100 | | TM200 | |
|---|---|---|---|---|
| Component | Rice Hulls Weight (lb)/1000 lb | Soy Hulls Weight (lb)/1000 lb | Rice Hulls Weight (lb)/1000 lb | Soy Hulls Weight (lb)/1000 lb |
| Oxytetracycline dihydrate | 234.3 | 237.9 | 468.6 | 475.7 |
| Calcium carbonate | 635.7 | 632.1 | 401.4 | 394.3 |
| Roughage | 80.0 | 80.0 | 80.0 | 80.0 |
| Mineral Oil | 50.0 | 50.0 | 50.0 | 50.0 |

It was established that the pH levels of 1.2 and 3.0 would be used for this study because these pH levels chosen reflected the gastric pH of monogastrics, generally acidic in a range of 1-4. In addition, previous data comparing solubility of the powder and granular material showed very little dissolution at pH 4.6 or pH 7.4 and oxytetracycline is generally more soluble in acidic environments.

The relative solubility of the Oxytetracycline formulations were established by comparing the Oxytetracycline solubility at two pH levels (1.2 and 3.0) for the time periods one, fifteen, and thirty minutes.

One sample of each formulation was used. Each sample was analyzed for Oxytetracycline content at each pH in duplicate. The samples were weighed and a known amount of pH buffer added. The samples were shaken on a reciprocating shaker for the specified amount of time at ambient temperature of about 22.5° C. The resulting sample solution was filtered into an autosampler vial and analyzed by HPLC for Oxytetracycline content. The results for the extracted (by the shaking procedure) samples were compared to the concentration of the as-received sample.

Standard Information

The following standards were used in this project.

TABLE 14

Assay Standards

| Compound | Lot Number | MPI ID | Purity |
|---|---|---|---|
| USP Oxytetracycline dihydrate | J1J172 | SP0013886 | 900 µg/mg |
| Tetracycline | 081M15982V | SP0013633 | 978 µg/mg |

Oxytetracycline dihydrate is used as the standard for assay.
Tetracycline is used as a resolution standard in system suitability.

Two pH buffers were prepared at 1.2 and 3.0 according to USP guidelines.

For each time point (1 minute, 15 minutes, 30 minutes and 2 hours), one 0.56 gram aliquot was weighed for each sample for each pH into a 250 mL plastic centrifuge bottle. Two hundred milliliters of pH 1.2 or pH 3.0 was added to each sample. The samples were placed on a reciprocating shaker for the designated amount of time. The pH of the sample solution was also recorded. Following the appropriate time period, a portion of each solution was filtered through an IC Acrodisc 0.45 µm syringe filter into an HPLC vial. The solutions were then analyzed in duplicate using method described herein.

The amount of Oxytetracycline found in each sample was calculated. In addition, a percent of premix assay was calculated by dividing the amount found in the shaken sample by the premix assay result and multiplying by 100%.

Premixes were analyzed with the following results Presented in Table 15:

TABLE 15

Premix Analysis

| Premix | Oxytetracycline HCl (g/lb) |
|---|---|
| TM 100 | 96.5 |
| TM 100 Rice Hulls | 103.5 |
| TM100 Soy Hulls | 100.2 |
| TM 200 | 178.9 |
| TM 200 Rice Hulls | 190.7 |
| TM200 Soy Hulls | 174.0 |

The analytical method is presented in subsequent paragraphs.

The amount of oxytetracycline that was dissolved in buffer solutions having a pH of 1.2 and 3.0 after extraction (shaken in buffer) for 1 min, 15 min, 30 min and 2 hours was determined and is given for each sample in the following tables.

The percent of premix assay was calculated by dividing the amount found in the shaken (extracted) sample by the premix assay result multiplied by 100. Because the amount of oxytetracycline in the three premixes at each concentration (i.e. TM100, TM100 rice hulls, TM100 soy hulls) differed, the percent of premix assay values are used to compare the quantity dissolved at the specific time points. At every point of comparison the granule with roughage dissolved faster than the associated granule without roughage. The percent of oxytetracycline HCl extracted is calculated by dividing the amount of oxytetracycline HCl in solution by the amount of oxytetracycline in the premix and the result multiplied by 100.

Dissolution Results

TABLE 16

1 Minute Extraction

| Sample ID | Soln. pH | Sample ID No. | Oxytetracycline HCl Extracted (g/lb) | Oxytetracycline HCl Extracted as Percent of Premix | Average of Oxytetracycline HCl Extracted as Percent of Premix |
|---|---|---|---|---|---|
| TM-100 w/rice hulls | 1.2 | 27654-0001 A | 90.9 | 87.8 | |
| TM-100 w/rice hulls | | 27654-0001 A | 90.9 | 87.8 | 87.8 |
| TM-100 w/out rice hulls | 1.2 | 27654-0002 A | 64.2 | 66.6 | |
| TM-100 w/out rice hulls | | 27654-0002 A | 64.2 | 66.6 | 66.6 |
| TM-200 w/rice hulls | 1.2 | 27654-0003 A | 194.0 | 101.7 | |
| TM-200 w/rice hulls | | 27654-0003 A | 193.3 | 101.4 | 101.6 |
| TM-200 w/outrice hulls | 1.2 | 27654-0004 A | 142.4 | 79.6 | |
| TM-200 w/out rice hulls | | 27654-0004 A | 143.0 | 79.9 | 79.8 |
| TM100 w/-Soy Hulls | | 28486-0001 A | 95.5 | 95.2 | |
| TM100 w/-Soy Hulls | 1.2 | 28486-0001 A | 95.1 | 94.9 | 95.1 |
| TM200 w/-Soy Hulls | | 28486-0003 | 170.3 | 97.9 | |
| TM200 w/-Soy Hulls | 1.2 | 28486-0003 | 170.7 | 98.1 | 98.0 |
| TM-100 w/rice hulls | 3.0 | 27654-0001 B | 24.5 | 23.6 | |
| TM-100 w/rice hulls | | 27654-0001 B | 23.9 | 23.1 | 23.4 |
| TM-100 w/out rice hulls | 3.0 | 27654-0002 B | 16.9 | 17.5 | |
| TM-100 w/out rice hulls | | 27654-0002 B | 16.6 | 17.2 | 17.4 |
| TM-200 w/rice hulls | 3.0 | 27654-0003 B | 68.0 | 35.6 | |
| TM-200 w/rice hulls | | 27654-0003 B | 67.2 | 35.2 | 35.4 |
| TM-200 w/out rice hulls | 3.0 | 27654-0004 B | 44.0 | 24.6 | |
| TM-200 w/out rice hulls | | 27654-0004 B | 43.9 | 24.6 | 24.6 |
| TM100 w/-Soy Hulls | 3.0 | 28486-0001 A | 23.5 | 23.5 | |
| TM100 w/-Soy Hulls | | 28486-0001 A | 23.4 | 23.4 | 23.5 |
| TM200 w/-Soy Hulls | 3.0 | 28486-0003 A | 46.1 | 26.5 | |
| TM200 w/-Soy Hulls | | 28486-0003 | 45.9 | 26.4 | 26.5 |

TABLE 17

15 Minute Extraction Results

| Sample ID | Soln. pH | Sample ID No. | Oxytetracycline HCl Extracted (g/lb) | Oxytetracycline HCl Extracted as Percent of Premix | Average of Oxytetracycline HCl Extracted as Percent of Premix |
|---|---|---|---|---|---|
| TM-100 w/rice hulls | 1.2 | 27654-0001 A | 103.7 | 100.2 | |
| TM-100 w/rice hulls | | 27654-0001 A | 103.9 | 100.4 | 100.3 |
| TM-100 w/out rice hulls | 1.2 | 27654-0002 A | 88.0 | 91.2 | |
| TM-100 w/out rice hulls | | 27654-0002 A | 88.0 | 91.2 | 91.2 |
| TM-200 w/rice hulls | 1.2 | 27654-0003 A | 192.6 | 101.0 | |
| TM-200 w/rice hulls | | 27654-0003 A | 191.4 | 100.4 | 100.7 |
| TM-200 w/out rice hulls | 1.2 | 27654-0004 A | 166.8 | 93.2 | |
| TM-200 w/out rice hulls | | 27654-0004 A | 169.1 | 94.5 | 93.9 |
| TM-100 w/-Soy Hulls | 1.2 | 28486-0001 A | 98.1 | 97.8 | |
| TM-100 w/-Soy Hulls | | 28486-0001 A | 98.7 | 98.4 | 98.1 |
| TM-200 w/-Soy Hulls | 1.2 | 28486-0003 A | 171.3 | 98.5 | |
| TM-200 w/-Soy Hulls | | 28486-0003 A | 171.2 | 98.4 | 98.5 |
| TM-100 w/rice hulls | 3.0 | 27654-0001 B | 47.3 | 45.7 | |
| TM-100 w/rice hulls | | 27654-0001 B | 47.2 | 45.6 | 45.7 |
| TM-100 w/out rice hulls | 3.0 | 27654-0002 B | 29.8 | 30.9 | |
| TM-100 w/out rice hulls | | 27654-0002 B | 29.8 | 30.9 | 30.9 |
| TM-200 w/rice hulls | 3.0 | 27654-0003 B | 84.5 | 44.3 | |
| TM-200 w/rice hulls | | 27654-0003 B | 85.3 | 44.7 | 44.5 |
| TM-200 w/out rice hulls | 3.0 | 27654-0004 B | 54.3 | 30.3 | |
| TM-200 w/out rice hulls | | 27654-0004 B | 54.1 | 30.2 | 30.3 |
| TM-100 w/-Soy Hulls | 3.0 | 28486-0001 B | 41.2 | 41.1 | |
| TM-100 w/-Soy Hulls | | 28486-0001 B | 41.1 | 41.0 | 41.1 |
| TM-200 w/-Soy Hulls | 3.0 | 28486-0003 B | 54.9 | 31.6 | |
| TM-200 w/-Soy Hulls | | 28486-0003 B | 55.0 | 31.6 | 31.6 |

TABLE 18

30 Minute Extraction Results

| Sample ID | Soln. pH | Sample ID No. | Oxytetracycline HCl Extracted (g/lb) | Oxytetracycline HCl Extracted as Percent of Premix | Average of Oxytetracycline HCl Extracted as Percent of Premix |
|---|---|---|---|---|---|
| TM-100 w/rice hulls | 1.2 | 27654-0001 A | 106.8 | 103.2 | |
| TM-100 w/rice hulls | | 27654-0001 A | 107.1 | 103.5 | 103.4 |
| TM-100 w/out rice hulls | 1.2 | 27654-0002 A | 90.7 | 94.0 | |
| TM-100 w/out rice hulls | | 27654-0002 A | 90.5 | 93.8 | 93.9 |
| TM-200 w/rice hulls | 1.2 | 27654-0003 A | 194.1 | 101.8 | |
| TM-200 w/rice hulls | | 27654-0003 A | 195.7 | 102.6 | 102.2 |
| TM-200 w/out rice hulls | 1.2 | 27654-0004 A | 175.3 | 98.0 | |
| TM-200 w/out rice hulls | | 27654-0004 A | 174.8 | 97.7 | 97.9 |
| TM-100 w/-Soy Hulls | 1.2 | 28486-0001 A | 103.9 | 103.7 | |
| TM-100 w/-Soy Hulls | | 28486-0001 A | 100.8 | 100.6 | 102.2 |
| TM-200 w/-Soy Hulls | 1.2 | 28486-0003 A | 171.8 | 98.7 | |
| TM-200 w/-Soy Hulls | | 28486-0003 A | 170.1 | 97.8 | 97.8 |
| TM-100 w/rice hulls | 3.0 | 27654-0001 B | 47.3 | 45.7 | |
| TM-100 w/rice hulls | | 27654-0001 B | 47.3 | 45.7 | 45.7 |
| TM-100 w/out rice hulls | 3.0 | 27654-0002 B | 36.9 | 38.2 | |
| TM-100 w/out rice hulls | | 27654-0002 B | 36.8 | 38.1 | 38.2 |
| TM-200 w/rice hulls | 3.0 | 27654-0003 B | 85.3 | 44.7 | |
| TM-200 w/rice hulls | | 27654-0003 B | 85.3 | 44.7 | 44.7 |
| TM-200 w/out rice hulls | 3.0 | 27654-0004 B | 66.5 | 37.2 | |
| TM-200 w/out rice hulls | | 27654-0004 B | 66.3 | 37.1 | 37.2 |
| TM-100 w/-Soy Hulls | 3.0 | 28486-0001 B | 53.7 | 53.6 | |
| TM-100 w/-Soy Hulls | | 28486-0001 B | 53.6 | 53.5 | 53.6 |
| TM-200 w/-Soy Hulls | 3.0 | 28486-0003 B | 67.5 | 38.8 | |
| TM-200 w/-Soy Hulls | | 28486-0003 B | 67.9 | 39.0 | 38.9 |

TABLE 19

| | | | | | Average of |
| | | | | Oxytetracycline | Oxytetracycline |
| | | | | HCl | HCl |
| | | | Oxytetracycline | Extracted as | Extracted as |
| Sample | Soln. | Sample | HCl Extracted | Percent of | Percent of |
| ID | pH | ID No. | (g/lb) | Premix | Premix |
|---|---|---|---|---|---|
| 2 Hour Extraction Results | | | | | |
| TM-100 w/rice hulls | 1.2 | 27654-0001 A | 105.8 | 102.2 | |
| TM-100 w/rice hulls | | 27654-0001 A | 107.0 | 103.4 | 102.8 |
| TM-100 w/out rice hulls | 1.2 | 27654-0002 A | 97.3 | 100.8 | |
| TM-100 w/out rice hulls | | 27654-0002 A | 97.5 | 101.0 | 100.9 |
| TM-200 w/rice hulls | 1.2 | 27654-0003 A | 193.6 | 101.5 | |
| TM-200 w/rice hulls | | 27654-0003 A | 193.5 | 101.4 | 101.5 |
| TM-200 w/out rice hulls | 1.2 | 27654-0004 A | 193.5 | 108.2 | |
| TM-200 w/out rice hulls | | 27654-0004 A | 189.5 | 105.9 | 107.1 |
| TM-100 w/- Soy Hulls | 1.2 | 28486-0001 A | 101.9 | 101.7 | |
| TM-100 w/- Soy Hulls | | 28486-0001 A | 100.5 | 100.3 | 101.0 |
| TM-200 w/- Soy Hulls | 1.2 | 28486-0003 A | 169.0 | 97.2 | |
| TM-200 w/- Soy Hulls | | 28486-0003 A | 169.5 | 97.4 | 97.3 |
| TM-100 w/rice hulls | 3.0 | 27654-0001 B | 66.6 | 64.3 | |
| TM-100 w/rice hulls | | 27654-0001 B | 66.9 | 64.6 | 64.5 |
| TM-100 w/out rice hulls | 3.0 | 27654-0002 B | 60.3 | 62.4 | |
| TM-100 w/out rice hulls | | 27654-0002 B | 60.5 | 62.7 | 62.6 |
| TM-200 w/rice hulls | 3.0 | 27654-0003 B | 92.5 | 48.5 | |
| TM-200 w/rice hulls | | 27654-0003 B | 92.2 | 48.3 | 48.4 |
| TM-200 w/out rice hulls | 3.0 | 27654-0004 B | 77.5 | 43.3 | |
| TM-200 w/out rice hulls | | 27654-0004 B | 77.3 | 43.2 | 43.3 |
| TM-100 w/- Soy Hulls | 3.0 | 28486-0001 B | 64.5 | 64.4 | |
| TM-100 w/- Soy Hulls | | 28486-0001 B | 66.5 | 66.4 | 65.4 |
| TM-200 w/- Soy Hulls | 3.0 | 28486-0003 B | 75.4 | 43.3 | |
| TM-200 w/- Soy Hulls | | 28486-0003 B | 75.2 | 43.2 | 43.3 |

TABLE 20

Extraction Sample Weights For the 1, 15, 30 and 2 Hour Extraction Studies

| Sample ID | Soln. pH | Sample ID No. | Sample Wt (g) |
|---|---|---|---|
| Minute Extraction | | | |
| TM-100 w/rice hulls | 1.2 | 27654-0001 A | 0.56109 |
| TM-100 w/rice hulls | | 27654-0001 A | 0.56109 |
| TM-100 w/out rice hulls | 1.2 | 27654-0002 A | 0.56097 |
| TM-100 w/out rice hulls | | 27654-0002 A | 0.56097 |
| TM-200 w/rice hulls | 1.2 | 27654-0003 A | 0.56175 |
| TM-200 w/rice hulls | | 27654-0003 A | 0.56175 |
| TM-200 w/out rice hulls | 1.2 | 27654-0004 A | 0.56128 |
| TM-200 w/out rice hulls | | 27654-0004 A | 0.56128 |
| TM100 w/-Soy Hulls | 1.2 | 28486-0001 A | 0.56075 |
| TM100 w/-Soy Hulls | | 28486-0001 A | 0.56075 |
| TM200 w/-Soy Hulls | 1.2 | 28486-0003 A | 0.56238 |
| TM200 w/-Soy Hulls | | 28486-0003 A | 0.56238 |
| TM-100 w/rice hulls | 3.0 | 27654-0001 B | 0.56154 |
| TM-100 w/rice hulls | | 27654-0001 B | 0.56154 |
| TM-100 w/out rice hulls | 3.0 | 27654-0002 B | 0.56070 |
| TM-100 w/out rice hulls | | 27654-0002 B | 0.56070 |
| TM-200 w/rice hulls | 3.0 | 27654-0003 B | 0.56093 |
| TM-200 w/rice hulls | | 27654-0003 B | 0.56093 |
| TM-200 w/out rice hulls | 3.0 | 27654-0004 B | 0.56052 |
| TM-200 w/out rice hulls | | 27654-0004 B | 0.56052 |
| TM100 w/-Soy Hulls | 3.0 | 28486-0001 B | 0.56057 |
| TM100 w/-Soy Hulls | | 28486-0001 B | 0.56057 |
| TM200 w/-Soy Hulls | 3.0 | 28486-0003 B | 0.56178 |
| TM200 w/-Soy Hulls | | 28486-0003 B | 0.56178 |
| 15 Minute Extraction | | | |
| TM-100 w/rice hulls | 1.2 | 27654-0001 A | 0.56098 |
| TM-100 w/rice hulls | | 27654-0001 A | 0.56098 |
| TM-100 w/out rice hulls | 1.2 | 27654-0002 A | 0.56057 |
| TM-100 w/out rice hulls | | 27654-0002 A | 0.56057 |
| TM-200 w/rice hulls | 1.2 | 27654-0003 A | 0.56118 |
| TM-200 w/rice hulls | | 27654-0003 A | 0.56118 |
| TM-200 w/out rice hulls | 1.2 | 27654-0004 A | 0.56042 |
| TM-200 w/out rice hulls | | 27654-0004 A | 0.56042 |
| TM100 w/-Soy Hulls | 1.2 | 28486-0001 A | 0.56040 |
| TM100 w/-Soy Hulls | | 28486-0001 A | 0.56040 |
| TM200 w/-Soy Hulls | 1.2 | 28486-0003 A | 0.56135 |
| TM200 w/-Soy Hulls | | 28486-0003 A | 0.56135 |
| TM-100 w/rice hulls | 3.0 | 27654-0001 B | 0.56096 |
| TM-100 w/rice hulls | | 27654-0001 B | 0.56096 |
| TM-100 w/out rice hulls | 3.0 | 27654-0002 B | 0.56166 |
| TM-100 w/out rice hulls | | 27654-0002 B | 0.56166 |
| TM-200 w/rice hulls | 3.0 | 27654-0003 B | 0.56199 |
| TM-200 w/rice hulls | | 27654-0003 B | 0.56199 |
| TM-200 w/out rice hulls | 3.0 | 27654-0004 B | 0.56102 |
| TM-200 w/out rice hulls | | 27654-0004 B | 0.56102 |
| TM100 w/-Soy Hulls | 3.0 | 28486-0001 B | 0.56010 |
| TM100 w/-Soy Hulls | | 28486-0001 B | 0.56010 |
| TM200 w/-Soy Hulls | 3.0 | 28486-0003 B | 0.56127 |
| TM200 w/-Soy Hulls | | 28486-0003 B | 0.56127 |
| 30 Minute Extraction | | | |
| TM-100 w/rice hulls | 1.2 | 27654-0001 A | 0.56116 |
| TM-100 w/rice hulls | | 27654-0001 A | 0.56116 |
| TM-100 w/out rice hulls | 1.2 | 27654-0002 A | 0.56033 |
| TM-100 w/out rice hulls | | 27654-0002 A | 0.56033 |
| TM-200 w/rice hulls | 1.2 | 27654-0003 A | 0.56171 |
| TM-200 w/rice hulls | | 27654-0003 A | 0.56171 |
| TM-200 w/out rice hulls | 1.2 | 27654-0004 A | 0.56081 |
| TM-200 w/out rice hulls | | 27654-0004 A | 0.56081 |
| TM100 w/-Soy Hulls | 1.2 | 28486-0001 A | 0.56169 |
| TM100 w/-Soy Hulls | | 28486-0001 A | 0.56169 |
| TM200 w/-Soy Hulls | 1.2 | 28486-0003 A | 0.56041 |
| TM200 w/-Soy Hulls | | 28486-0003 A | 0.56041 |
| TM-100 w/rice hulls | 3.0 | 27654-0001 B | 0.56113 |
| TM-100 w/rice hulls | | 27654-0001 B | 0.56113 |
| TM-100 w/out rice hulls | 3.0 | 27654-0002 B | 0.56165 |
| TM-100 w/out rice hulls | | 27654-0002 B | 0.56165 |
| TM-200 w/rice hulls | 3.0 | 27654-0003 B | 0.56138 |
| TM-200 w/rice hulls | | 27654-0003 B | 0.56138 |
| TM-200 w/out rice hulls | 3.0 | 27654-0004 B | 0.56044 |
| TM-200 w/out rice hulls | | 27654-0004 B | 0.56044 |
| TM100 w/-Soy Hulls | 3.0 | 28486-0001 B | 0.56130 |
| TM100 w/-Soy Hulls | | 28486-0001 B | 0.56130 |
| TM200 w/-Soy Hulls | 3.0 | 28486-0003 B | 0.56118 |
| TM200 w/-Soy Hulls | | 28486-0003 B | 0.56118 |
| 2 Hour Extraction | | | |
| TM-100 w/rice hulls | 1.2 | 27654-0001 A | 0.56110 |
| TM-100 w/rice hulls | | 27654-0001 A | 0.56110 |
| TM-100 w/out rice hulls | 1.2 | 27654-0002 A | 0.56072 |
| TM-100 w/out rice hulls | | 27654-0002 A | 0.56072 |
| TM-200 w/rice hulls | 1.2 | 27654-0003 A | 0.56125 |
| TM-200 w/rice hulls | | 27654-0003 A | 0.56125 |
| TM-200 w/out rice hulls | 1.2 | 27654-0004 A | 0.56115 |
| TM-200 w/out rice hulls | | 27654-0004 A | 0.56115 |
| TM100 w/-Soy Hulls | 1.2 | 28486-0001 A | 0.56086 |
| TM100 w/-Soy Hulls | | 28486-0001 A | 0.56086 |
| TM200 w/-Soy Hulls | 1.2 | 28486-0003 A | 0.56087 |
| TM200 w/-Soy Hulls | | 28486-0003 A | 0.56087 |
| TM-100 w/rice hulls | 3.0 | 27654-0001 B | 0.56159 |
| TM-100 w/rice hulls | | 27654-0001 B | 0.56159 |
| TM-100 w/out rice hulls | 3.0 | 27654-0002 B | 0.56063 |
| TM-100 w/out rice hulls | | 27654-0002 B | 0.56063 |
| TM-200 w/rice hulls | 3.0 | 27654-0003 B | 0.56141 |
| TM-200 w/rice hulls | | 27654-0003 B | 0.56141 |
| TM-200 w/out rice hulls | 3.0 | 27654-0004 B | 0.56099 |
| TM-200 w/out rice hulls | | 27654-0004 B | 0.56099 |
| TM100 w/-Soy Hulls | 3.0 | 28486-0001 B | 0.56110 |
| TM100 w/-Soy Hulls | | 28486-0001 B | 0.56110 |
| TM200 w/-Soy Hulls | 3.0 | 28486-0003 B | 0.56065 |
| TM200 w/-Soy Hulls | | 28486-0003 B | 0.56065 |

The weights for the extraction samples for tables 16-19 are contained in Table 20.

The results of the solubility experiments are graphically presented in FIGS. 2 to 5.

Conclusions

At all time points the granular premixes containing the roughage displayed a higher level of dissolution than the granular premix without the roughage. At every time point the Oxytetracycline dissolved to a specific level, i.e. pH 1.2 showed 100% dissolution and pH 3.0 dissolved to approx. 40% to 60% of the total inclusion in the granule. The 2 and 6 hour data demonstrate that ultimately both the granules with and without roughage provide the same amount of oxytetracycline to the animal, however, the granules containing the roughage provide the level of oxytetracycline faster.

Assay procedure for the determination of oxytetracycline content in premixes by
HPLC Procedure
Chromatographic Conditions:
Column: Hamilton PRP-1 (250 mm.×4.6 mm, 7 μm)
Mobile phase: 20% acetonitrile/80% ultra pure water containing 0.5 g 1-hexane sulfonic acid sodium salt per liter of mobile phase. The mobile phase pH is adjusted to pH=2 using concentrated sulfuric acid.
Detection: 270 nm
Flow rate: 1.5 ml/min
Column temp.: Ambient
Injection volume: 20 μl
Run time: 10 min.
Preparation of Standard Solutions:
Oxytetracycline Analytical Standard Solution:
Accurately weigh 50 mg (+/−5 mg) of the oxytetracycline reference standard into a 100 ml volumetric flask.

Add 50 ml of 0.1 M methanolic hydrochloric acid to the volumetric flask. Then place this flask in an ultrasonic bath and sonicate until dissolution is apparent.

Remove the volumetric flask from the ultrasonic bath. Allow the contents of the flask to cool to room temperature and dilute to volume with ultra pure water. This is the oxytetracycline analytical standard stock solution. This stock solution is stable for up to 3 days at room temperature and 7 days if stored in a refrigerator.

Concentration of this standard is nominally 500 μg/ml and should be adjusted for the potency of the reference standard and the actual weight of the standard.

Oxytetracycline Calibration Standard:

Prepare dilutions of the standard stock solution in 0.01 M aqueous hydrochloric acid as below and mix thoroughly.

TABLE 21

Calibration Standards.

| Calibration Standard Identification | Approximate Final Concentration μg/ml |
|---|---|
| Calibration Standard # 1 | 25 |
| Calibration Standard # 2 | 50 |
| Calibration Standard # 3 | 100 |
| Calibration Standard # 4 | 150 |
| Calibration Standard # 5 | 200 |

Tetracycline Stock Standard Solution:

Accurately weigh 20 mg (+/−5 mg) of the tracycline reference standard into a 100 ml volumetric flask.

Add 50 ml of 0.1 M methanolic hydrochloric acid to the volumetric flask. Then place this flask in an ultrasonic bath and sonicate until dissolution is apparent.

Remove the volumetric flask from the ultrasonic bath. Allow the contents of the flask to cool to room temperature and dilute to volume with ultra pure water. This is the oxytetracycline analytical standard stock solution. This stock solution is stable for up to 7 days if stored in a refrigerator.

Concentration of this standard is nominally 200 μg/ml and should be adjusted for the potency of the reference standard and the actual weight of the standard.

Resolution Standard Solution:

Prepare a resolution standard solution in 0.1 M aqueous hydrochloric acid having a nominal oxytetracycline concentration of about 100 μg/ml and a nominal tetracycline concentration of about 20 μg/ml.

Preparation of Dry Test Samples:

Accurately weigh and transfer an appropriate amount of sample to a 500 ml. volumetric flask. For Terramycin 200, Oxytetracycline 200 g/lb, sample size is about 1.0 g for a volume of 500 ml. Add 250 ml of 0.1 M methanolic hydrochloric acid to the flask. Place this volumetric flask in an ultrasonic bath and sonicate for 20 minutes, shake this flask frequently during the sonication period to aid dissolution. After this time, remove the volumetric flask from the ultrasonic bath, cool to room temperature and then add 200 ml of ultra pure water.

Allow the contents of the flask to cool to room temperature after the addition of the water, then dilute to volume with ultra pure water and mix thoroughly. Filter approximately 10 ml of this solution through a 0.2-0.5 micron disposable syringe filter, discarding the first 2 ml, into a 50 ml plastic screw cap centrifuge tube.

Transfer 5.0 ml of this solution to a 50 ml volumetric flask. Dilute to volume using 0.01 M aqueous hydrochloric acid and then mix thoroughly. Sample solutions are stable for up to 7 days at room temperature and refrigerated temperature.

Preparation of Dissolution Samples:

Allow the contents of the dissolution flask to cool to room temperature. Filter approximately 10 ml of this solution through a 0.2-0.5 micron disposable syringe filter, discarding the first 2 ml, into a 50 ml plastic screw cap centrifuge tube. Transfer 5.0 ml of this solution to a 50 ml volumetric flask. Dilute to volume using 0.01 M aqueous hydrochloric acid and then mix thoroughly. Sample solutions are stable for up to 7 days at room temperature and refrigerated temperature.

Using a five point standard curve, determine the amount of oxytetracycline in each sample to be tested.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined in the appended claims.

We claim:

1. A particulate animal feed supplement, comprising particles having a nominal particle size of from 1800 μm to 50 μm, wherein the particles comprise rice hulls, calcium carbonate and oxytetracycline.

2. A particulate animal feed supplement prepared by the process comprising the steps of:
   forming a composition comprising rice hulls and calcium carbonate;
   adding oxytetracycline to the composition to form a mixture;
   mixing until the mixture is uniform;
   compacting the mixture to form a solid material;
   milling the solid material to form particles; and
   screening the particles to obtain particles having a particle size from 1000 μm to 50 μm.

3. The supplement of claim 2 wherein the rice hulls are present in an amount of from about 2% to about 25% by weight of the supplement.

4. The supplement of claim 2 wherein the calcium carbonate is present in an amount of from about 10% to about 80% by weight of the supplement.

5. The supplement of claim 2 wherein the oxytetracycline is present in an amount of from about 1% to about 60% by weight of the supplement.

6. The supplement of claim 2 further comprising an anti-dusting agent.

7. The supplement of claim 6 wherein the anti-dusting agent is selected from the group consisting of mineral oil, soybean oil and a combination thereof.

8. The supplement of claim 6, wherein the anti-dusting agent is present in an amount of from greater than 0% to 10% by weight of the supplement.

9. The supplement of claim 6 wherein the anti-dusting agent is present in an amount of from about 1% to about 7% by weight of the supplement.

10. The particulate animal feed supplement of claim 2, wherein the oxytetracycline is added to the mixture while mixing.

11. A particulate animal feed supplement prepared by the process comprising the steps of:
- forming a composition comprising rice hulls and calcium carbonate;
- adding mineral oil, and oxytetracycline, or a salt, metal complex or hydrate thereof, to the composition simultaneously or in any order to form a mixture;
- mixing until the mixture is uniform;
- compacting the mixture to form a solid material;
- milling the solid material to form particles; and
- screening the particles to obtain particles having a particles size from 1000 μm to 50 μm.

12. The supplement of claim 11 wherein the salt comprises an acid addition salt.

13. The supplement of claim 11 wherein the rice hulls are present in an amount of from about 2% to about 25% by weight of the supplement.

14. The supplement of claim 11 wherein the calcium carbonate is present in an amount of from about 10% to about 80% by weight of the supplement.

15. The supplement of claim 11 wherein the oxytetracycline, or salt, metal complex or hydrate thereof, is present in an amount of from about 1% to about 60% by weight of the supplement.

16. The supplement of claim 11, wherein the mineral oil is present in an amount of from greater than 0% to 10% by weight of the supplement.

17. The supplement of claim 16 wherein the mineral oil is present in an amount of from about 1% to about 7% by weight of the supplement.

18. The supplement of claim 11, wherein the oxytetracycline, or salt, metal complex or hydrate thereof, is added to the mixture while mixing.

19. A method 23, comprising:
- forming a uniform mixture by adding oxytetracycline to a mixture of rice hulls and calcium carbonate while mixing;
- compacting the uniform mixture to form a solid material; and
- obtaining particles by milling the solid material and screening, the particles having a size of from 1800 μm to 50 μm.

* * * * *